United States Patent
Zevallos et al.

(10) Patent No.: US 10,540,482 B2
(45) Date of Patent: Jan. 21, 2020

(54) NFC TAG READER FOR PATIENT MEDICATION MONITORING

(71) Applicants: Juan Zevallos, Miami, FL (US); Ravi Shankar, Boca Raton, FL (US); Santiago Aguerrevere, Boca Raton, FL (US)

(72) Inventors: Juan Zevallos, Miami, FL (US); Ravi Shankar, Boca Raton, FL (US); Santiago Aguerrevere, Boca Raton, FL (US)

(73) Assignee: The Florida International University Board of Trustees, Miami, FL (US)

( * ) Notice: Subject to any disclaimer, the term of this patent is extended or adjusted under 35 U.S.C. 154(b) by 201 days.

(21) Appl. No.: 15/644,449

(22) Filed: Jul. 7, 2017

(65) Prior Publication Data

US 2018/0011987 A1     Jan. 11, 2018

Related U.S. Application Data

(60) Provisional application No. 62/359,383, filed on Jul. 7, 2016.

(51) Int. Cl.
| | |
|---|---|
| *G06F 19/00* | (2018.01) |
| *G06K 19/07* | (2006.01) |
| *G16H 40/63* | (2018.01) |
| *H04B 1/3827* | (2015.01) |
| *G06Q 10/10* | (2012.01) |

(52) U.S. Cl.
CPC ..... *G06F 19/3462* (2013.01); *G06K 19/0716* (2013.01); *G16H 40/63* (2018.01); *G06Q 10/1093* (2013.01); *H04B 1/3827* (2013.01)

(58) Field of Classification Search
CPC .. G06F 19/3462; G07F 17/0092; G07F 11/62; G07G 1/009; G16H 40/67; G16H 20/13; G16H 40/63; G06K 19/0716; A61J 1/03; G06Q 10/1093; H04B 1/3827
See application file for complete search history.

(56) References Cited

U.S. PATENT DOCUMENTS

| | | | |
|---|---|---|---|
| 2008/0054007 A1* | 3/2008 | Mador | A61J 7/0481 221/1 |
| 2014/0263423 A1* | 9/2014 | Akdogan | A61J 7/0076 222/23 |
| 2015/0051730 A1* | 2/2015 | Portney | H04W 4/70 700/242 |
| 2015/0106369 A1* | 4/2015 | Nolan | G06F 16/9535 707/732 |
| 2015/0237461 A1* | 8/2015 | Goyal | H04B 1/385 455/41.2 |
| 2015/0310185 A1* | 10/2015 | Shah | G06F 19/3462 340/10.6 |

(Continued)

*Primary Examiner* — Lewis G West
(74) *Attorney, Agent, or Firm* — Saliwanchik, Lloyd & Eisenschenk

(57) ABSTRACT

Systems and devices for regulation of self-management of a medication schedule are provided. A system can include a pill dispenser cap, a plurality of insulating layers; a near field communication (NFC) tag, and a pill dispenser. The system can further include a graphical user interface (GUI), and first and second mobile devices each having a display unit, a sensor, a processor, and a computer readable medium.

9 Claims, 3 Drawing Sheets

(56) References Cited

U.S. PATENT DOCUMENTS

| | | | |
|---|---|---|---|
| 2015/0360834 A1* | 12/2015 | Mikhail | B65D 51/248 |
| | | | 340/384.5 |
| 2016/0232327 A1* | 8/2016 | Windridge | G06F 19/3456 |
| 2016/0324726 A1* | 11/2016 | Roberts | A61J 7/02 |
| 2016/0327427 A1* | 11/2016 | Briones | A61J 7/02 |
| 2017/0235919 A1* | 8/2017 | Bauss | G06F 19/3462 |
| | | | 705/2 |
| 2017/0312183 A1* | 11/2017 | Wilson | A61J 7/0084 |
| 2018/0064609 A1* | 3/2018 | Hines | G16H 40/63 |
| 2018/0280245 A1* | 10/2018 | Khalid | G08B 21/24 |
| 2019/0105235 A1* | 4/2019 | Seo | A61J 7/0436 |

\* cited by examiner

NFC TAG READER FOR PATIENT MEDICATION MONITORING

CROSS-REFERENCE TO RELATED APPLICATION

This application claims the benefit of U.S. Provisional Application Ser. No. 62/359,383, filed Jul. 7, 2016, which is incorporated herein by reference in its entirety, including any figures, tables, and drawings.

BACKGROUND

Medical professionals and patients can collaborate to create a personalized medication schedule to optimize therapeutic benefits and recovery. Self-administration of medication provides patients with a level of autonomy and personal investment in a treatment plan. Patients may be motivated to successfully participate in the plan; however cognitive abilities, competing priorities, and physical well-being can hinder performance.

Medical professionals require effective tools and systems to determine a patient's compliance with a medication schedule. Mobile software devices can be coupled with certain devices to assist doctors in effectively monitoring patients who self-manage their medication schedules.

BRIEF SUMMARY

Embodiments of the subject inventions can track the number of doses a patient takes of any given medication. The number of doses and the dosage times can be recorded by a patient through use of current mobile device technology coupled with an integrated pill bottle dispenser described herein. Information can be retrieved from the pill dispenser and transmitted to and monitored by a medical professional or automated system. By leveraging existing mobile device technology, patients can transmit information to their medical professional and demonstrate compliance with a particular schedule.

In some embodiments, an integrated pill bottle can emit a first signal to alert a patient that the time to take medication is approaching. The system can then emit a second signal to alert the patient that the time to take medication has arrived. The second signal can continue to emit until the patient opens and reseals the integrated pill bottle.

Embodiments of the subject invention provide methods for monitoring of patient self-management. Medical professionals can register an integrated pill bottle to a particular patient and medication. The pill bottle can provide an alarm to alert the patient that medicine should be taken. The patient can further register a time, date, and location of taking the medication without manually inputting any data.

DETAILED DESCRIPTION

Figure 1:
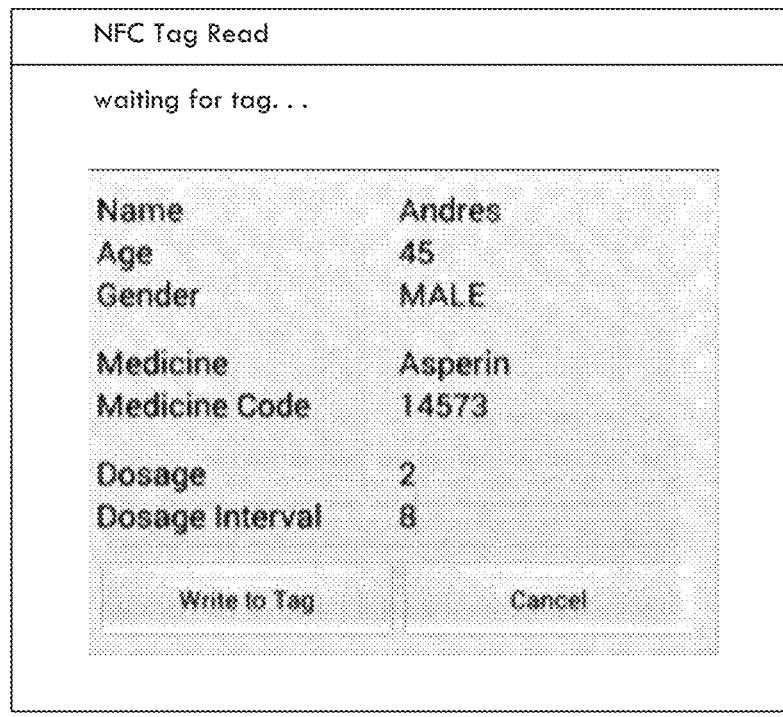
FIG. 1 shows an image of a display from a graphical user interface, according to an embodiment of the subject invention.

Embodiments of the subject invention provide novel and advantages devices, systems, and methods that enable patients to communicate medication compliance with their medical professional. Effectiveness of patient self-medication can be improved and physicians can receive real time reports to remotely monitor pill taking. A patient's adherence to a medication regimen can be monitored in order to effectively correlate a patient's progress with the treatment plan. The system and devices can provide audio and visual signals, without involvement from medical personnel, to alert patients to take medication. Increasing the effectiveness of current self-medication methods enables patients to better control chronic/acute disease (such as diabetes or heart disease) in order to avoid further complications. The modular design of the devices described herein allows NFC tag compatibility with multiple versions of pill dispenser caps. Additionally, the systems, devices, and methods described herein are medication independent allowing large scale deployment.

Near field communication (NFC) is a wireless communication technology that enables devices to transmit and receive encoded information. NFC technology is spreading through retail industry, commercial transaction, and social networking disciplines to replace traditional bar code technology and allow more efficient transfer of information.

NFC tags are passive devices in that they store information, but do not possess separate power sources or processing capabilities. The NFC tags operate and are powered by electromagnetic induction, according to Faraday's law. A source device can propagate a fluctuating magnetic field by transmitting an alternating current through a transmitting coil. The alternating current induces a magnetic field in a perpendicular direction of the electrical current. The strength of the magnetic field can be adjusted through increasing or decreasing the number of turns of the coil or modulating the electrical current through the coil. The fluctuating magnetic field can induce an electrical current in a nearby receiving coil. The electrical current flows in a perpendicular direction of the magnetic field.

An NFC tag comprises a coil and a computer readable medium capable of storing encoded bits of data. NFC tags can be purchased with encoded information or blank to allow a user to write in data with the assistance of an NFC writer. The majority of modern smart phones are equipped with NFC technology that enables them to power and communicate with an NFC tag. Modern smartphones typically display an "N" letter icon on a home screen to alert a user that the device contains NFC technology.

In some embodiments, systems and methods can comprise program instructions (e.g., mobile application software) that allow encoded bits of patient data to be written to and read by an NFC tag. The written data can include patient name, age, emergency contacts, gender, medication name, medication code, dosage, and interval. NFC tags have different storage capacities and the size of the NFC tag can be dependent upon a maximum amount of data written to the NFC tag. The program instructions (e.g., mobile application software) can: (1) enable medical personnel to register a particular NFC tag to a particular patient; (2) enter and review patient's case information and history; (3) allow a patient to enter dosage times; and (4) transmit the information from a patient's mobile device to the appropriate medical personnel.

In certain embodiments of the subject invention, a doctor can interact with a mobile user interface to register a particular NFC tag to a particular patient. Additionally, the doctor can restrict usage with a password to prevent unauthorized use of the application. Once initializing the application, the doctor can press a "Write" button, upon which the doctor can be prompted to input patient and medication information. The application can allow a medical professional to enter a patient's name, age, sex, medication, medication code, dosage, and dosage interval, as seen in FIG. 1. After the information is entered, the doctor can press a "Write Tag" button and place an NFC tag underneath the NFC writing device until the writing is complete. The medical personnel can then place the NFC tag into an underside of a cap of a pill dispenser and provide the integrated dispenser to a patient.

Multiple tags can be written with different information, unless they are not rewritable, in which case a new tag can be written in when the medication is given to the patient.

Figure 2:
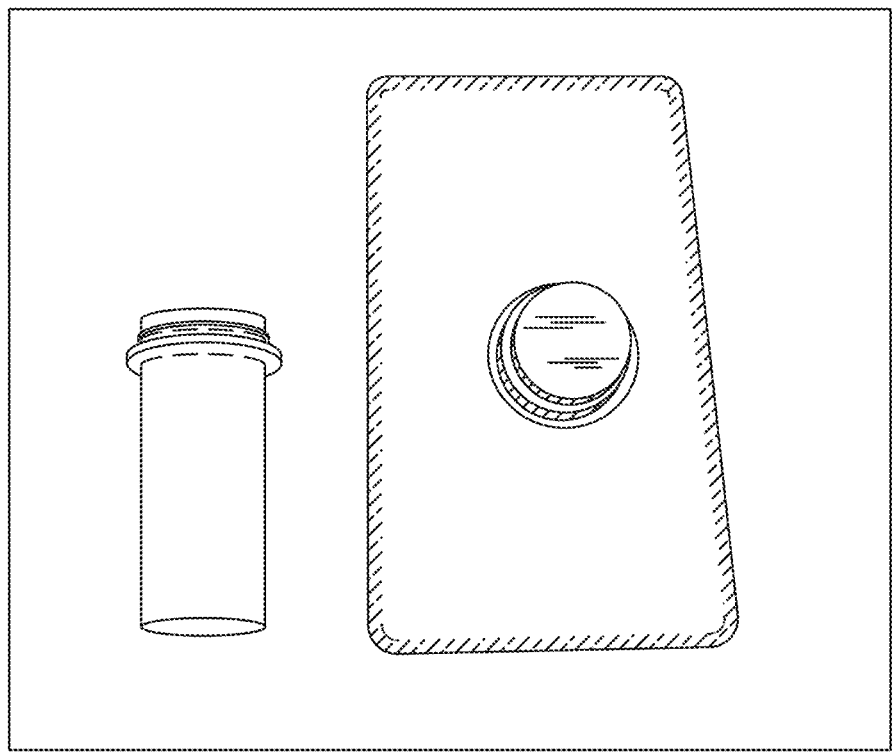
FIG. 2 shows an image of an integrated pill dispenser cap positioned above an NFC chip on a mobile device.

A patient can use their own personal mobile device to transmit a signal back to the system that a medication dose has been taken. A patient can unlock the cap from the dispenser and remove a pill. The patient can then expose the NFC tag to an NFC tag reader in the mobile device by exposing the cap's underside to the mobile device, as seen in FIG. 2. By placing the exposed portion of the NFC tag on the bottom of the cap, the patient has to open the dispenser in order for the system to detect the NFC tag. When the NFC chip within the mobile device is in close proximity to the NFC tag, the mobile device can transfer power through electromagnetic indication to the tag and the NFC reader can read the tag. The mobile application can retrieve information encoded in the NFC tag, such as the patient's name, medication, and dosage interval. The mobile application can additionally retrieve information from the mobile device such as the date, time and location that the NFC tag has been read.

In an embodiment of the subject invention, the program instructions (e.g., mobile application software) can detect the mobile device type and display a visual image of the mobile device with a graphical icon to displays where the NFC chip on the mobile device is located in order to position the tag correctly.

After the mobile device has retrieved information from the NFC tag, the program instructions (e.g., mobile application software) can transmit the information, through a server, to the appropriate medical personal. The program instructions (e.g., mobile application software) can comprise a library of medication codes and recommended dosage time intervals. The program instructions (e.g., mobile application software) can compare an individual's dosage pattern with a recommended or customized dosage schedule. If a patient is ingesting medication too frequently or infrequently, the program instructions (e.g., mobile application software) can alert the appropriate medical personnel, emergency contacts, and the patient. This innovative feature adds an additional layer of security for patients self-managing their medication regimen.

Figure 3:
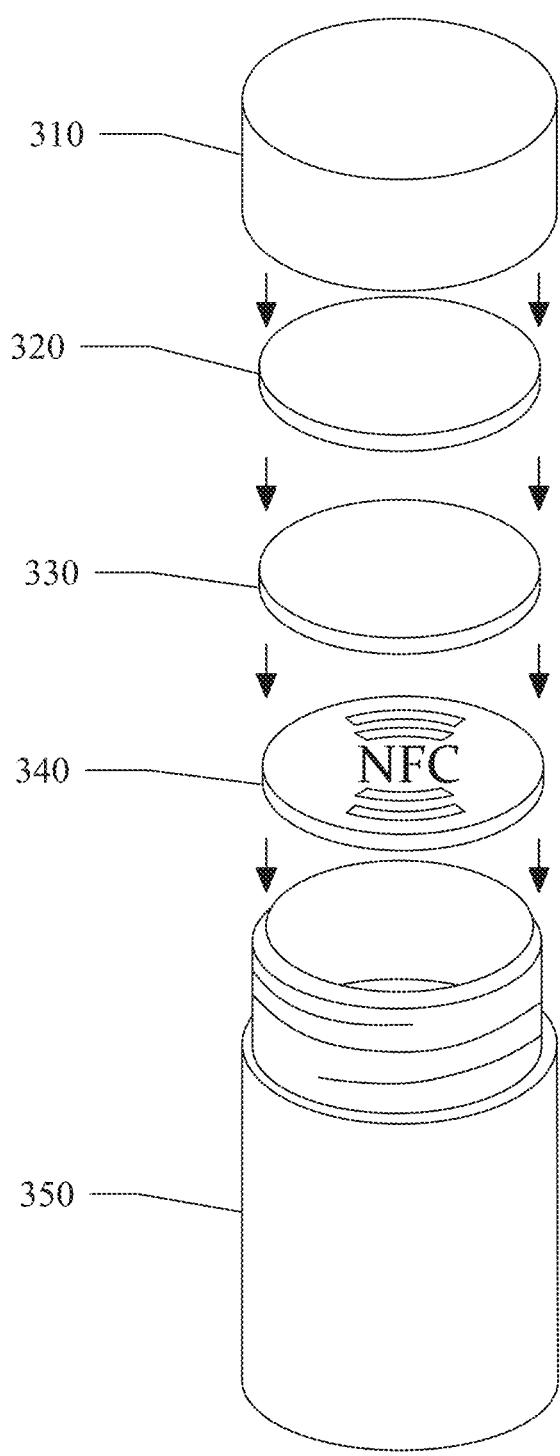
FIG. 3 shows an exploded view of an integrated near field communication (NFC) tag pill dispenser, according to an embodiment of the subject invention.

Referring to FIG. 3, in some embodiments, an NFC tag embedded pill dispenser comprises: an NFC tag 340, a first insulating material (for example, a washer) 320, a second insulating material (for example, foam) 330, a cap 310, and a dispenser 350. The first insulating material 320 can be disposed between a bottom surface of the pill cap 310 and a top surface of the second insulating material 330. The first insulating material 320 prevents or inhibits an NFC tag reader from detecting a signal from a top surface of the cap 310. In order to prevent or inhibit patients from falsely or unintentionally transmitting information to a mobile device, the NFC tag 340 can be configured such that it only transmits information when an NFC tag 340 is exposed from the bottom of a cap 310. This additional safety feature forces a patient to open the pill dispenser in order for an NFC tag reader to retrieve information. The second insulating material 330 can be disposed between the first insulating material 320 and the NFC tag 340. The second insulating material 330 provides spatial separation from the first insulating material 320 and prevents or inhibits the first insulating material 320 from interfering with a signal transmission from the NFC tag 340 to the NFC tag reader.

In an embodiment of the subject invention, the program instructions (e.g., mobile application software) can have a library of recommended medication schedules or enable a medical professional to engineer a personalized schedule based upon the needs of a patient. The program instructions (e.g., mobile application software) can transmit the medication schedule to the integrated pill dispenser. As the time to take a patients medicine nears, the integrated pill dispenser can begin to emit and audio or visual warning signal. The signal can be configured to continue emitting until such time that the pill dispenser is opened. At such time after the pill dispenser is closed, a second signal can be emitted to indicate that the required dosage has successfully been taken.

Figure 4:
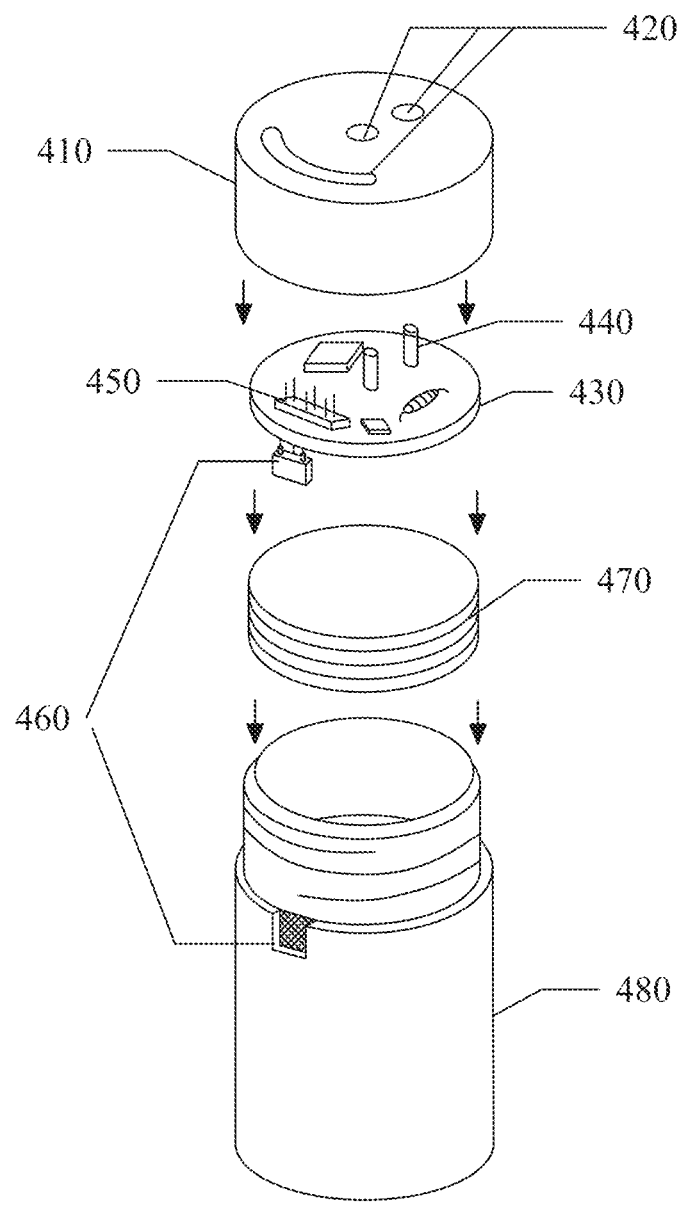
FIG. 4 shows an exploded view of an exploded view of an integrated NFC tag and sensor pill dispenser, according to an embodiment of the subject invention.

In an embodiment, the integrated pill dispenser comprises a cap, a printed circuit board (PCB) embedded with electrical circuitry, a sensor, a plurality of insulating materials, an NFC tag, and a power source. Referring to FIG. 4, a cap 410 can be configured to contain a plurality of apertures 420. A PCB 430 can comprise a plurality of signal producing sources 440 (for example, light emitting diodes (LEDs)) that emit light through apertures 420 in the cap 410, a processor, and a male or female electrical connector 450 (for example, pin connections). The electrical connector 450 can be configured to allow access through a third aperture 420 in the cap 410. An NFC layer 470 can be disposed at a bottom surface of the PCB, in which the NFC layer 470 comprises a plurality insulating layers and an NFC tag, and the NFC tag can be disposed on a bottom side of the NFC layer 470 to be exposed from an underside of the cap 410. The PCB 430 can further be connected to a sensor 460 (for example, a Hall effect sensor) configured to detect the opening and resealing of the cap 410 onto the pill dispenser 480.

The signal sources 440 can be configured to emit light at different frequencies or wavelengths to producing different colors of light emitted at various intervals. The program instructions (e.g., mobile application software) can transmit a schedule of medication intervals to the integrated pill dispenser. If a patient has not the prescribed medication at the appropriate time, the pill dispenser can emit a green light for a predetermined period of time. After the time has expired, the green light can cease and a red light can be emitted for an indefinite period of time. The processor can be configured to detect the removal of the cap 410 from the dispenser 480. The signal source 440 can continue to emit red light to remind the patient to reseal the dispenser 480. The processor can be further configured to detect that the cap 410 has sealed back on the dispenser 480. At such time, the red light ceases to emit and the cycle can be repeated for the next time the patient is required to take medication.

In another embodiment of the subject invention, the PCB 430 can be connected to at least one audio producing source. This would enable a person with poor or no eyesight to better regulate their self-medication schedule.

In an embodiment of the subject invention, the program instructions (e.g., mobile application software) can be further configured to alert medical personal, the patient, or emergency contacts if the patient's actual medication schedule deviates from an approved medication schedule.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes, but is not limited to, the following exemplified embodiments.

Embodiment 1

A device for regulation of self-management of a medication schedule, the device comprising:
a pill dispenser cap comprising a top surface and a bottom surface;
a first insulating layer comprising a top surface and a bottom surface;
a second insulating layer comprising a top surface and a bottom surface;
a near field communication (NFC) tag disposed at a bottom surface of the second insulating material; and
a pill dispenser.

Embodiment 2

The device of embodiment 1, in which the top surface of the first insulating material is disposed at the bottom surface of the cap.

Embodiment 3

The device according to any of embodiments 1-2, in which the top surface of the second insulating material is disposed at the bottom surface of the first insulating material.

Embodiment 4

The device according to any of embodiments 1-3, in which the NFC tag is configured to only receive and emit a signal from a bottom surface of the NFC tag.

Embodiment 5

The device according to any of embodiments 1-4, in which the first insulating material is configured to prevent or inhibit a signal from emitting from a top surface of the NFC tag.

Embodiment 6

The device according to any of embodiments 1-5, in which the second insulating material is configured to prevent or inhibit the first insulating material from interfering with the NFC tag receiving or emitting a signal.

Embodiment 7

The device according to any of embodiments 1-6, in which the NFC tag is encoded with bits of data that convey a unique identity of a subject in need of medication, a medication name, medication code of dosage, and dosage interval.

Embodiment 8

The device according to any of embodiments 1-7, further comprising a sensor, a processor, a plurality of signal producing sources, a power source, a computer readable medium, and an electrical connector.

Embodiment 9

The device according to embodiment 8, in which each signal producing source of the plurality of signal producing sources comprises a light emitting source.

Embodiment 10

The device according to any of embodiments 8-9, in which each signal producing source of the plurality of signal producing sources comprises an audio emitting source.

Embodiment 11

A system for regulation of self-management of a medication schedule, the system comprising:
the device of claim 1;
a first mobile device comprising a first display unit, a first processor, and a first computer readable medium;
a second mobile device comprising a second display unit, a second processor, and a second computer readable medium;
program instructions for executing commands when directed to do so by a processor (e.g., mobile application software); and
a graphical user interface (GUI).

Embodiment 12

The system according to embodiment 11, in which the first mobile device is configured to detect the NFC tag, write to the NFC tag, and read the NFC tag.

Embodiment 13

The system according to any of embodiments 11-12, in which the second mobile device is configured to detect the NFC tag and read the NFC tag.

Embodiment 14

The system according to any of embodiments 11-13, in which the program instructions (e.g., mobile application software) are configured to permit a user of the first mobile device to use the GUI to write information to the NFC tag, regarding patient identification and medication, and receive information from the second mobile device.

Embodiment 15

The system according to any of embodiments 11-14, in which the program instructions (e.g., mobile application software) are configured to permit a user of the first mobile device to receive patient and medication information from the second mobile device.

Embodiment 16

The system according to any of embodiments 11-15, in which the mobile application is configured to permit a user of the second mobile to detect an NFC tag, read an NFC tag, and transmit information encoded onto the NFC tag, including the date, the time, and the location.

Embodiment 17

The system according to embodiment 16, wherein the device further comprises a sensor, a third processor, a plurality of signal producing sources, a power source, a third computer readable medium, and an electrical connector, in which the program instructions (e.g., mobile application software) are configured to transmit a medication schedule to the third computer readable medium, and induce at least one of the plurality of signal generating sources to emit a warning signal for a predetermined period of time.

Embodiment 18

The system according to embodiment 17, in which the third processor is configured to detect if the cap has been removed or replaced, in which the third processor is configured to terminate emission of the warning signal upon replacement of the cap.

Embodiment 19

A method of regulation of self-management of a medication schedule, the method comprising:
using a mobile software application to write information regarding a subject in need of a medication's identity and the medication's identity to a near field communication (NFC) tag;
embedding the NFC tag into a cap of a device as described in any of embodiments 1-10;
providing the device to a subject in need of medication;
exposing the NFC tag to a mobile device equipped with an NFC reader;
retrieving the subject in need's identity and the medication's identity from the NFC tag;
retrieving a date, a time, and a location from the mobile device; and
transmitting the retrieved information to a medical professional.

Embodiment 20

The method according to embodiment 19, further comprising encoding the device with a medication schedule, emitting a first signal when the time to take medication is approaching, and ceasing to emit the first signal when the time to take medication has arrived.

Embodiment 21

The method according to embodiment 20, further comprising emitting a second signal when the time to take medication has arrived, sensing the removal of the cap of the device, sensing the resealing of the cap of the device, and ceasing emission of the second signal when the cap is resealed.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section, if present) are incorporated by reference in their entirety, including all figures and tables, to the extent they are not inconsistent with the explicit teachings of this specification.

What is claimed is:

1. A device for regulation of self-management of a medication schedule, the device comprising:
a pill dispenser cap comprising a top surface and a bottom surface;
a plurality of insulating layers comprising a first insulating layer and a second insulating layer;
a near field communication (NFC) tag comprising a top surface and a bottom surface; and
a pill dispenser,
the first insulating layer comprising a top surface and a bottom surface,
the top surface of first insulating layer being directly connected to the bottom surface of the cap,
the second insulating layer comprising a top surface and a bottom surface,
the top surface of second insulating layer being directly connected to the bottom surface of the first insulating layer, and
the top surface of the NFC tag being directly connected to the bottom surface of the second insulating layer.

2. The device according to claim 1, the NFC tag being configured to only receive and emit a signal from the bottom surface of the NFC tag.

3. The device according to claim 1, the first insulating material being configured to inhibit a signal from emitting from the top surface of the NFC tag.

4. The device according to claim 1, the second insulating material being configured to inhibit the first insulating material from interfering with the NFC tag receiving or emitting a signal.

5. The device according to claim 1, the NFC tag being encoded with bits of data that convey an identity of a subject in need of medication, a medication, a medication code, a dosage, and a dosage interval.

6. The device according to claim 1, further comprising a sensor, a processor, a plurality of signal producing sources, a power source, a computer readable medium, and an electrical connector.

7. The device according to claim 6, in which each signal producing source of the plurality of signal producing sources comprises a light emitting source.

8. The device according to claim 6, in which each signal producing source of the plurality of signal producing sources comprises an audio emitting source.

9. The device according to claim 6, in which the sensor comprises a Hall Effect sensor.

\* \* \* \* \*